US010512702B2

(12) United States Patent
O'Donnell et al.

(10) Patent No.: US 10,512,702 B2
(45) Date of Patent: Dec. 24, 2019

(54) BREATHING ASSISTANCE APPARATUS

(71) Applicant: Fisher & Paykel Healthcare Limited, Auckland (NZ)

(72) Inventors: Kevin Peter O'Donnell, Auckland (NZ); Matthew Jon Payton, Auckland (NZ); Christopher Simon James Quill, Auckland (NZ); Martin Paul Friederich Kramer, Auckland (NZ); Peter Geoffrey Hawkins, Auckland (NZ); Reena Daken, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 38 days.

(21) Appl. No.: 15/388,481

(22) Filed: Dec. 22, 2016

(65) Prior Publication Data

US 2017/0100501 A1  Apr. 13, 2017

Related U.S. Application Data

(63) Continuation of application No. 14/181,368, filed on Feb. 14, 2014, now Pat. No. 9,526,807, which is a
(Continued)

(30) Foreign Application Priority Data

Dec. 15, 2005 (NZ) .......................... 544169

(51) Int. Cl.
*A61L 2/24* (2006.01)
*A61M 16/00* (2006.01)
(Continued)

(52) U.S. Cl.
CPC .................. *A61L 2/24* (2013.01); *A61B 5/01* (2013.01); *A61B 5/4836* (2013.01); *A61L 2/06* (2013.01);
(Continued)

(58) Field of Classification Search
CPC ...... A61L 2/24; A61M 16/109; A61M 16/024
See application file for complete search history.

(56) References Cited

U.S. PATENT DOCUMENTS 3,893,458 A  7/1975 Fletcher et al.
4,110,419 A  8/1978 Miller
(Continued)

FOREIGN PATENT DOCUMENTS

JP         4352965    12/1992
JP       H08-252314   10/1996
(Continued)

OTHER PUBLICATIONS

Translated Office Action in corresponding Japanese Application No. 2008-545524, dated Dec. 7, 2011, 4 pages.
(Continued)

*Primary Examiner* — Kevin Joyner
(74) *Attorney, Agent, or Firm* — Knobbe Martens Olson & Bear, LLP

(57) ABSTRACT

The present invention provides a breathing assistance apparatus that has a convenient and effective method of cleaning internal conduits inside the apparatus. The breathing assistance apparatus is preferably a gases supply and humidification device. The cleaning method is a method of disinfection that is automated so minimal training is required to disinfect in particular an internal elbow conduit within the device. It is therefore not necessary to dismantle the gases supply and humidification device, therefore, inadvertent damage to the internal parts of the device is avoided. The present invention also provides a method of disinfecting a heated breathing conduit and a patient interface.

25 Claims, 9 Drawing Sheets

Related U.S. Application Data continuation of application No. 12/138,594, filed on Jun. 13, 2008, now Pat. No. 8,741,220, which is a continuation-in-part of application No. PCT/NZ2006/000330, filed on Dec. 15, 2006.

(51) Int. Cl.
*A61M 16/10* (2006.01)
*A61L 2/06* (2006.01)
*A61M 16/06* (2006.01)
*A61M 16/16* (2006.01)
*A61B 5/01* (2006.01)
*A61B 5/00* (2006.01)
*A61M 16/08* (2006.01)

(52) U.S. Cl.
CPC .... *A61M 16/0051* (2013.01); *A61M 16/0057* (2013.01); *A61M 16/0066* (2013.01); *A61M 16/0666* (2013.01); *A61M 16/0683* (2013.01); *A61M 16/0875* (2013.01); *A61M 16/109* (2014.02); *A61M 16/1075* (2013.01); *A61M 16/1095* (2014.02); *A61M 16/16* (2013.01); *A61L 2202/14* (2013.01); *A61L 2202/24* (2013.01); *A61M 2205/3368* (2013.01); *A61M 2205/502* (2013.01); *A61M 2205/52* (2013.01); *A61M 2209/10* (2013.01)

(56) References Cited

U.S. PATENT DOCUMENTS

| 5,696,686 A * | 12/1997 | Sanka .................. A61L 2/24 700/110 |
|---|---|---|
| 6,283,132 B1 | 9/2001 | Stephens et al. |
| 6,523,538 B1 | 2/2003 | Wikefeldt |
| 2004/0079370 A1 | 4/2004 | Gradon et al. |
| 2004/0261797 A1 | 12/2004 | White et al. |

FOREIGN PATENT DOCUMENTS

| JP | H08-299307 | 11/1996 |
| JP | 2001-321443 | 11/2001 |
| JP | 2002-345965 | 12/2002 |
| JP | 2005-40589 | 2/2005 |
| WO | WO 2004/024429 | 3/2004 |
| WO | WO 2004/026382 | 4/2004 |
| WO | WO 2005/011785 A1 | 2/2005 |
| WO | WO 2005/021076 | 3/2005 |
| WO | WO 2006/126900 | 11/2006 |

OTHER PUBLICATIONS

Japanese Examination Report with English Translation; dated Jun. 9, 2014; 4 pages.

* cited by examiner

BREATHING ASSISTANCE APPARATUS

This application is a continuation of U.S. application Ser. No. 14/181,368, filed Feb. 14, 2014, which is a continuation of U.S. application Ser. No. 12/138,594, filed Jun. 13, 2008, which is a continuation-in-part of PCT/NZ2006/000330, entitled "Breathing Assistance Apparatus," which has an international filing date of Dec. 15, 2006, which was published in English on Jun. 21, 2007 under International Publication Number WO 2007/069922, which claims priority of New Zealand Patent No. 544169, filed on Dec. 15, 2005, all of which are hereby incorporated by reference in their entirety.

BACKGROUND

Field of the Invention

This invention relates to a gases supply and gases humidification apparatus that can be disinfected and reused for different patients. The invention also relates to a method for disinfecting apparatus parts that extend the life of these parts for use by a single patient.

Description of the Related Art

A number of methods are known in the art for assisting a patient's breathing. Continuous Positive Airway Pressure (CPAP) involves the administration of air under pressure to a patient, usually by a nasal mask. It is used in the treatment of snoring and Obstructive Sleep Apnoea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

CPAP is also commonly used for patients with a variety of respiratory illnesses, including Chronic Obstructive Pulmonary Disease (COPD).

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment. An individual pressure is determined for each patient using CPAP and this pressure is set at the patient interface. Changes in nasal resistance affect pressure delivered to the pharynx and if the changes are of sufficient magnitude there may be recurrence of snoring or airway collapse or reduce the level of pressure applied to the lungs. Such symptoms can also occur in a hospital environment where a patient is on a respirator. Typically in such situations the patient is intubated. Therefore the throat tissue may become irritated and inflamed causing both distress to the patient and possible further respiratory problems.

A number of methods may be employed to treat such upper airway symptoms, including pharmacological agents to reduce nasal disease, or heating the bedroom. One most commonly employed method is humidification of the inspired air using an in line humidifier. Two types of humidifier are currently used. Cold pass-over humidifiers rely on humidifying the air through exposure to a large surface area of water. While they are cheap, the humidity output is low at high flows, typically 2 to 4 mg/L absolute humidity at flows above 25 L/min. The output is insufficient to prevent mucosal drying. Heated water bath humidifiers are more efficient, and produce high levels of humidity even at high flow rates. They are effective at preventing upper airway mucosal drying, prevent increases in nasal resistance, and are the most reliable means of treating upper airway symptoms. Oxygen is the most common drug prescribed to hospitalized patients. The delivery of oxygen via nasal cannula or facemask is of benefit to a patient complaining of breathlessness. By increasing the fraction of inspired oxygen, oxygen therapy reduces the effort to breathe and can correct resulting hypoxia (a low level of oxygen in the tissues).

The duration of the therapy depends on the underlying illness. For example, postoperative patients may only receive oxygen while recovering from surgery while patients with COPD require oxygen 16 to 18 hours per day.

Currently greater than 16 million adults are afflicted with COPD, an umbrella term that describes a group of lung diseases characterized by irreversible airflow limitation that is associated mainly with emphysema and chronic bronchitis, most commonly caused by smoking over several decades. When airway limitation is moderately advanced, it manifests as perpetual breathlessness, without physical exertion. Situations such as a tracheobronchial infection, heart failure and also environmental exposure can incite an exacerbation of COPD that requires hospitalization until the acute breathlessness is under control. During an acute exacerbation of COPD, the patient experiences an increase in difficulty of breathing (dyspnea), hypoxia, and increase in sputum volume and purulence and increased coughing.

Oxygen therapy provides enormous benefit to patients with an acute exacerbation of COPD who are hypoxic, by decreasing the risk of vital organ failure and reducing dyspnea. The major complication associated with oxygen therapy is hypercapnia (an elevation in blood carbon dioxide levels) and subsequent respiratory failure. Therefore, the dose of oxygen administered can be critical and must be precisely known.

To accurately control the oxygen dose given to a patient, the oxygen-enriched gas must exceed the patient's peak inspiratory flow to prevent the entrainment of room air and dilution of the oxygen. To achieve this, flows of greater than 20 L/min are common. Such flows of dry gases cause dehydration and inflammation of the nasal passages and airways if delivered by nasal cannula. To avoid this occurrence, a heated humidifier is used.

The majority of systems that are used for oxygen therapy or merely delivery of gases to a patient consists of a gases supply, a humidifier and conduit. Interfaces include facemasks, oral mouthpieces, tracheostomy inlets and nasal cannula, the latter having the advantage of being more comfortable and acceptable than a facemask.

A group of patients who would benefit from humidification therapy are patients who have mucociliary clearance deficiencies. These patients often have purulent mucus and are susceptible to infections from pathogens.

Heated humidified air with an abundance of water particles is an ideal medium to harbour disease carrying pathogens. Consequently, considerable design expertise has been required to provide the market with active pass-over humidifiers that deliver water molecules, in gas phase only, so that it is not possible for disease pathogens to be carried in air to the patient. Water that condenses on the inner surfaces of the breathing circuit or conduit at the end of a treatment session may harbour pathogens that would be delivered to the patient next time they use the device. This is particularly the case with humidification therapies where patients are receiving body temperature fully saturated air.

In hospital environments or similar it is often not possible for gases supply devices, such as devices that deliver CPAP and include a humidifier, to be used by multiple patients. If devices were to be used in this manner all parts, from the humidification chamber to and including the patient interface, must be disposed of or cleaned to a high standard of disinfection in between use by different patients. Often CPAP devices and humidifiers are provided in an integrated unit, such as the Sleepstyle™ 600 series CPAP device of Fisher & Paykel Healthcare Limited. This CPAP device is predominantly used for home use by an individual. This device has internal tubing from the outlet of the humidification chamber that is difficult to disinfect. As these devices are difficult to disinfect they are often not used in settings such as hospitals or clinics where multiple patients will use the device.

In the home use situation when oxygen therapy and CPAP devices are used by a single patient the lifespan of the breathing tube and patient interface is determined by the mechanical lifespan of the parts and the build up of microbial pathogens on the breathing gases path of these parts. Often it is hard to lower microbial contamination on the breathing gas surfaces of these parts.

SUMMARY

It is an object of the present invention to provide a breathing assistance apparatus which goes some way to overcoming the abovementioned disadvantages or which at least provides the public or industry with a useful choice.

Accordingly in a first aspect the invention may broadly be said to consist in a breathing assistance apparatus adapted to deliver humidified gases to a patient comprising: a housing including an atmospheric inlet adapted to allow gases to enter said housing, a gases supply within said housing, a gases supply outlet port in said housing, said gases supply outlet port in fluid connection with said gases supply and adapted to in use make fluid connection with the inlet of a humidifier of the type that includes both an inlet and an outlet, in order to supply gases to said humidifier via said inlet, a patient return in said housing, adapted to make fluid connection with said humidifier outlet in use in order to receive humidified gases from said humidifier in use, a patient outlet on said housing, in use in fluid connection with said patient return and also in fluid connection or adapted to make fluid connection with a breathing conduit for delivery of humidified gases to a patient, a first disinfection conduit including a heating element, said first disinfection conduit adapted for connection between said gases supply outlet port and said patient outlet, a controller in said housing adapted to supply power to the heating elements of conduits connected to said breathing assistance apparatus, said controller adapted to supply power to said first disinfection conduit when said first disinfection conduit is connected between said gases supply outlet port and said 'patient outlet so as to heat the flow of gases through said first disinfection conduit to keep said flow of gases at a predetermined temperature over a set period of time, said controller simultaneously supplying power to said gases supply so as to provide a flow of gases through said first disinfection conduit.

Preferably said breathing assistance apparatus further includes a temperature sensor located at or close to said patient return, said temperature sensor adapted to sense the temperature of gases flowing between said patient return and said patient outlet in use.

Preferably said controller is adapted to receive temperature data from said temperature sensor, said controller supplying power to said disinfection conduit so that temperatures between said patient return and said patient outlet reach a level of between 60° C. and 90° C. for a time period of approximately 20 minutes.

Preferably said controller provides a flow of gases through said disinfection conduit at a flow rate of approximately 10 litres per minute.

Preferably said breathing assistance apparatus further includes a second disinfection conduit adapted for connection between said patient return and a point at or close to said atmospheric inlet, said controller supplying power to said second disinfection conduit when said second disinfection conduit is connected between said patient return and said point at or close to said atmospheric inlet so as to heat the flow of gases through said second disinfection conduit to keep said flow of gases at a predetermined temperature over a set period of time, said controller simultaneously supplying power to said gases supply so as to provide a flow of gases through said second disinfection conduit, at least part of said supply of gases from said second disinfection conduit entering said atmospheric inlet.

Preferably said controller is further adapted to count and log the number of disinfection cycles that have taken place.

Preferably said apparatus further includes a filter connectable to said patient return to filter gases exiting said patient return.

Preferably said filter includes a projection adapted to increase the gases velocity where said gases exit said patient return.

In a second aspect the invention may broadly be said to consist in a method of disinfecting a breathing assistance apparatus of the type that has both an atmospheric inlet, a gases supply outlet port, a separate patient outlet and a patient return, and which includes a gases supply capable of supplying a flow of gases at a predetermined pressure from said gases supply outlet port, and which also includes a controller to supply power to the heating elements of conduits connected to said breathing assistance apparatus, said method comprising the steps of: connecting a first heated gases disinfection conduit between said gases supply outlet port and said patient outlet, said heated gases disinfection conduit of the type that includes a heating element, providing a predetermined circulating flow of gases to said heated gases disinfection conduit from said gases outlet for a predetermined period of time, heating said heating element up to a predetermined temperature to heat the gases passing through said heated gases disinfection conduit.

Preferably said predetermined period of time is between 20 and 40 minutes.

Preferably said predetermined temperature is between 60 and 90 degrees Celsius.

Preferably said predetermined circulating flow is between 5 and 20 litres per minute.

Preferably said method further includes the step of connecting a second disinfecting conduit between said patient return and a point at or close to said atmospheric inlet.

Preferably said predetermined period of time is between 20 and 40 minutes.

Preferably said predetermined temperature is between 60 and 90 degrees Celsius.

Preferably said predetermined circulating flow is between 5 and 20 litres per minute.

In a third aspect the invention may broadly be said to consist in a method of disinfecting at least one of a breathing conduit and patient interface, said breathing conduit being connected to a breathing assistance apparatus of the type that includes a gases supply capable of supplying a flow of gases at a predetermined pressure or flow to a patient via said breathing conduit, and which is also capable of providing power to said breathing conduit, said breathing assistance apparatus including a humidifying chamber and a heater capable of heating said chamber and said breathing conduit including a heating element, said breathing assistance apparatus further including a controller adapted to supply power to said heater and said heating element, said method comprising the steps of: removing said water from said chamber and replacing said chamber on said apparatus, providing a predetermined flow of gases from said gases supply to said chamber and at least one of said breathing conduit and patient interface over a predetermined period of time, powering said heater and said heating element to heat said gases supplied to said at least one of said breathing conduit and patient interface to a predetermined temperature to dry and disinfect said at least one of said breathing conduit and patient interface so as to prevent accumulation of bacteria in said at least one of said breathing conduit and patient interface.

Preferably said predetermined period of time is between 70 and 90 minutes.

Preferably said predetermined temperature is between 40° C. and 75° C.

Preferably said patient interface is connected to said conduit, so that gases supplied to said conduit also pass through said interface to dry and disinfect said patient interface.

Preferably said patient interface is not connected to said conduit, and said method includes the step of placing a cap on the patient end of said breathing conduit before said heated gases are caused to flow in said breathing conduit.

Preferably said method also includes the step of partly filling said chamber with a disinfecting agent and replacing said partly filled chamber on said breathing assistance apparatus before providing a predetermined flow of gases and powering said heater.

Preferably said method includes the step of housing said patient interface in a receptacle.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

A preferred form of the present invention will now be described with reference to the accompanying drawings.

DETAILED DESCRIPTION

The present invention provides a breathing assistance apparatus that can be cleaned and sterilised easily and effectively. The present invention also provides a convenient and effective method for cleaning the internal structure of the internal structure of the apparatus, and the conduits and interfaces used to provide gases to a user or patient.

Figure 1:
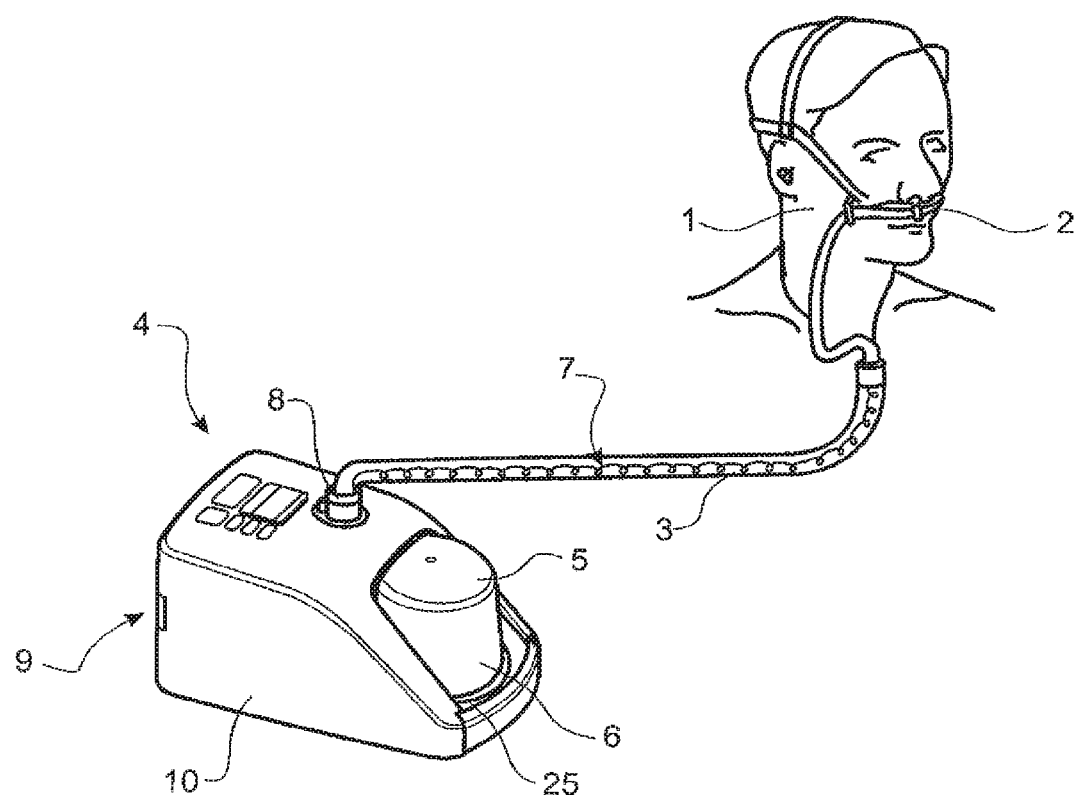
FIG. 1 is an illustration of a breathing assistance apparatus that forms a breathing circuit in use, the breathing assistance apparatus including a blower unit, a humidifier chamber, a delivery conduit and a patient interface, the blower unit including a heater plate for heating the contents of the humidifier chamber, the breathing assistance apparatus suitable for utilising the methods of disinfection of the present invention.

As shown in FIG. 1, in a preferred form of the invention, a flow of gases is provided to a patient by a breathing circuit 100. In the preferred form, the gases pass in sequence through the following elements of the system 100: a gases supply generator or flow driver 4 (such as a blower, fan or compressor), a humidification chamber 5, a heated delivery conduit or inspiratory conduit 3, and a patient interface 2.

Gases are passed to the patient by way of the patient interface 2. The patient interface 2 used with the apparatus of the present invention may be a full-face mask, nasal mask, nasal cannula, oral mouthpiece or tracheostomy connection, but the preferred embodiments as described below, and the Figures, describe and show a nasal cannula.

Figure 2:
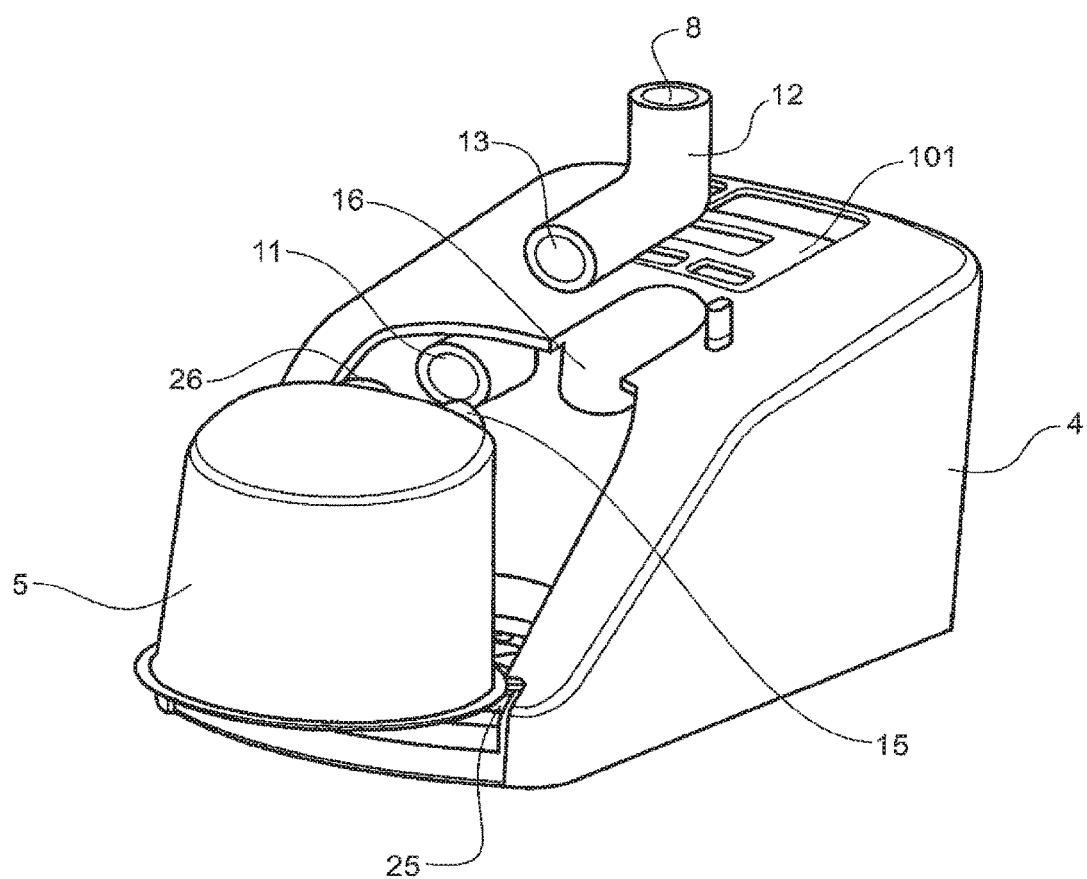
FIG. 2 is an exploded view of an elbow connection conduit of the breathing assistance apparatus of FIG. 1, the elbow connection conduit having a patient return end and a patient outlet end.

The patient 1 as shown in FIG. 1 is receiving humidified and pressurized gases through a nasal cannula 2. The cannula 2 is connected to the gases transportation pathway or inspiratory conduit 3 that in turn is connected to an integrated gases supply or blower 4, which in the preferred form includes a humidification chamber 5. In the preferred embodiment of the blower 4, the blower 4 is contained in one housing with the humidification chamber 5 rigidly coupled or connected to this in use. The humidification chamber 5 extends out from the housing 10 and is capable in use of being removed and replaced (by a slide on movement, such as that described in WO04024429 of Fisher & Paykel Healthcare Limited, the contents of which are incorporated by reference) by the patient or other user. The blower 4 includes a gases supply outlet port 11, as shown in FIG. 2, that feeds the inlet 26 of the humidification chamber 5. The inner end of the gases supply outlet port 11 is internal to the casing or housing 10 of the blower unit 4. In use, the humidification chamber 5 contains a volume of water 6. It must be appreciated that the embodiment described above in relation to the integrated blower and humidifier merely illustrates one form of the housing of the integrated gases supply and humidifying device. A modular system in which the blower unit and the humidifier unit are separate items could also be used.

The inspiratory conduit 3 is connected to a patient outlet 8 on the casing 10 of the blower unit 4. In the most preferred form of the invention, inspiratory conduit 3 contains heater wires 7 that heat the walls of the inspiratory conduit 3 to reduce condensation of humidified gases within the conduit 3 and the patient interface 2.

In the preferred form, the humidification chamber 5 is formed from a plastics material and has a highly heat conductive base (for example an aluminium base). The blower unit includes a heater plate 25, with the heat conductive base of the humidifier unit in contact with the heater plate 25 in use. The blower unit 4 is provided with an electronic controller 200 that in the preferred form comprises a microprocessor-based controller 200 executing computer software commands stored in an associated memory 201. The controller 200 is contained within the housing 10. The controller 200 receives input from sources such as a dial (not shown) or other user controls such as controls 101, through which a user 1 of the device 4 may, for example, set a predetermined required value (preset value) of humidity or temperature of the gases supplied to patient 1 by the breathing circuit 100.

The controller 200 may in some forms receive other inputs. For example, data from temperature sensors or similar at a point or points in the system 100. Using these input and the internal programming, the controller 200 determines when (or to what level) to energise heater plate 25 to heat the water 6 within humidification chamber 5. As the volume of water 6 within humidification chamber 5 is heated, water vapour begins to fill the volume of the chamber 5 above the surface of the water 6. As gases enter the chamber through inlet 26, pass through the vapour space above the water 6, and exit the chamber through chamber outlet 15, they become heated and humidified. The flow of gases (for example air) is provided from the blower unit 4. If the gases used are entirely sourced from atmosphere, the gases enter the device 4 through atmospheric inlet 9, which in the preferred form is located on the back of the device 4. It should be noted that at least a portion of the gases provided to a user by the system 100 could be oxygen, sourced from e.g. a wall-mounted port on a hospital wall or similar. This is useful if the user 1 is undergoing oxygen therapy and requires gases that include at least a fraction of oxygen.

The blower unit 4 preferably includes an internal variable speed pump or fan that draws air or other gases through the blower inlet 9. The speed of variable speed pump or fan is preferably controlled by the controller 200, the speed of the fan varying in response to commands received by the controller 200, the controller 200 varying these commands in relation to inputs entered into the device 4 by the user, and in the most preferred form, from data received from sensors located in the system 100. The fan provides a gases flow throughout the system. The power drawn by the fan can be used by the controller 200 to calculate the flow rate through the system, the controller 200 using a look-up table, simple calculation algorithm, or similar to find the flow rate that corresponds to a particular rate of power draw.

Disinfection of the Elements of the System

A partially exploded view of the blower unit 4 and humidification chamber 5 is shown in FIG. 2. The blower unit 4 of the preferred embodiment includes an elbowed connection conduit or elbow conduit 12. One end of the elbowed elbow conduit 12 forms patient outlet end 8, to which one end of the conduit 3 is connected in use. The other end forms a patient return 13, which is a gases return from the humidifier chamber 5 to the housing 10 of the blower unit 4. The elbow conduit 12 is adapted so that in use chamber outlet 15 connected with the patient return 13 so that the elbow conduit 12 receives humidified gases from the humidification chamber 5. The humidified gases are then directed from the patient outlet 8 into the breathing conduit 3 for delivery to patient 1. It is preferred that the elbow conduit 12 is permanently fixed in place in the housing 4.

In some instances, there will be a requirement for multiple users to use at least the blower unit 4, as they will be used in hospitals, sleep laboratories or leased by home care companies and hospitals for short term home users.

In order for the blower unit 4 to be safe for use on multiple patients the elbow conduit 12 must be disinfected to a high degree between different patients. For ease of use, it is preferred that the elbow conduit 12 is disinfected in situ. This ensures that even if the elbow conduit 12 can be removed, dismantling and potential damage to the internal parts of the device 4 can be avoided. This is preferred, as it is often impractical to remove the elbow, as it may include electrical connectors or similar, and therefore it is preferred that removal and reconnection as part of a cleaning process can be avoided. Furthermore, the high labour content and skill level required would make removing the elbow an unreliable cleaning method and may make the device more unreliable.

Currently high level disinfection is performed either by thermal or chemical process. Thermal disinfection is normally carried out by submersion in hot water or steam and chemical disinfection by submersion in instrument grade disinfectants. These processes have disadvantages for high level disinfection of devices such as the blower unit 4 of the present invention as it cannot be submersed, steam sterilized, or easily chemically disinfected.

Figure 3:
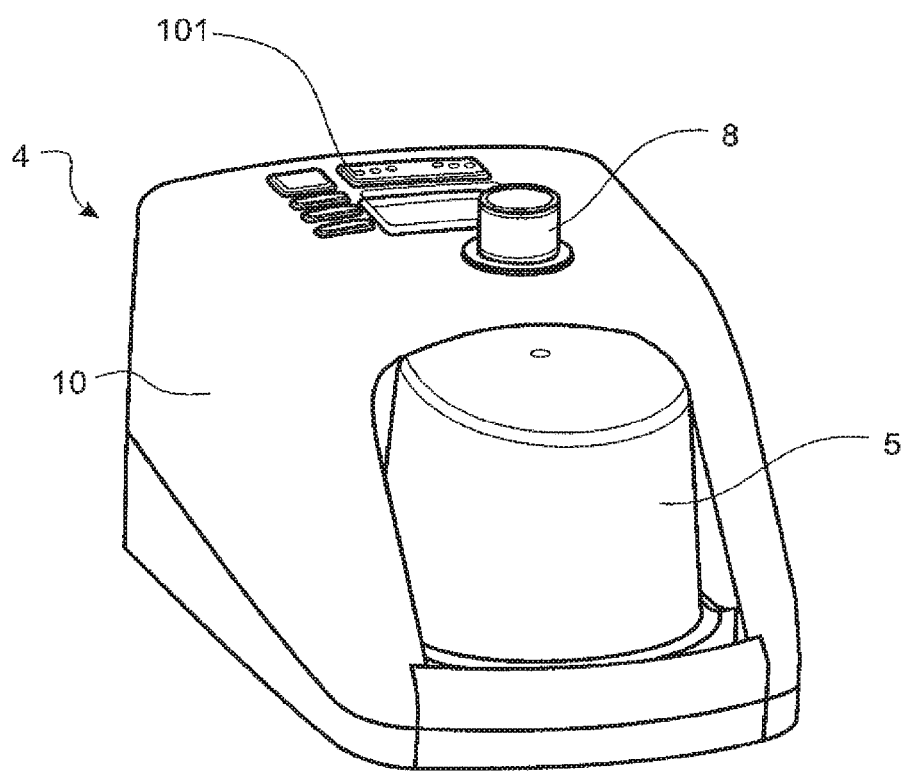
FIG. 3 is a perspective front view of the blower unit and humidifier chamber of FIG. 1 or FIG. 2, showing the humidifier chamber in place on the blower unit.
Figure 4:
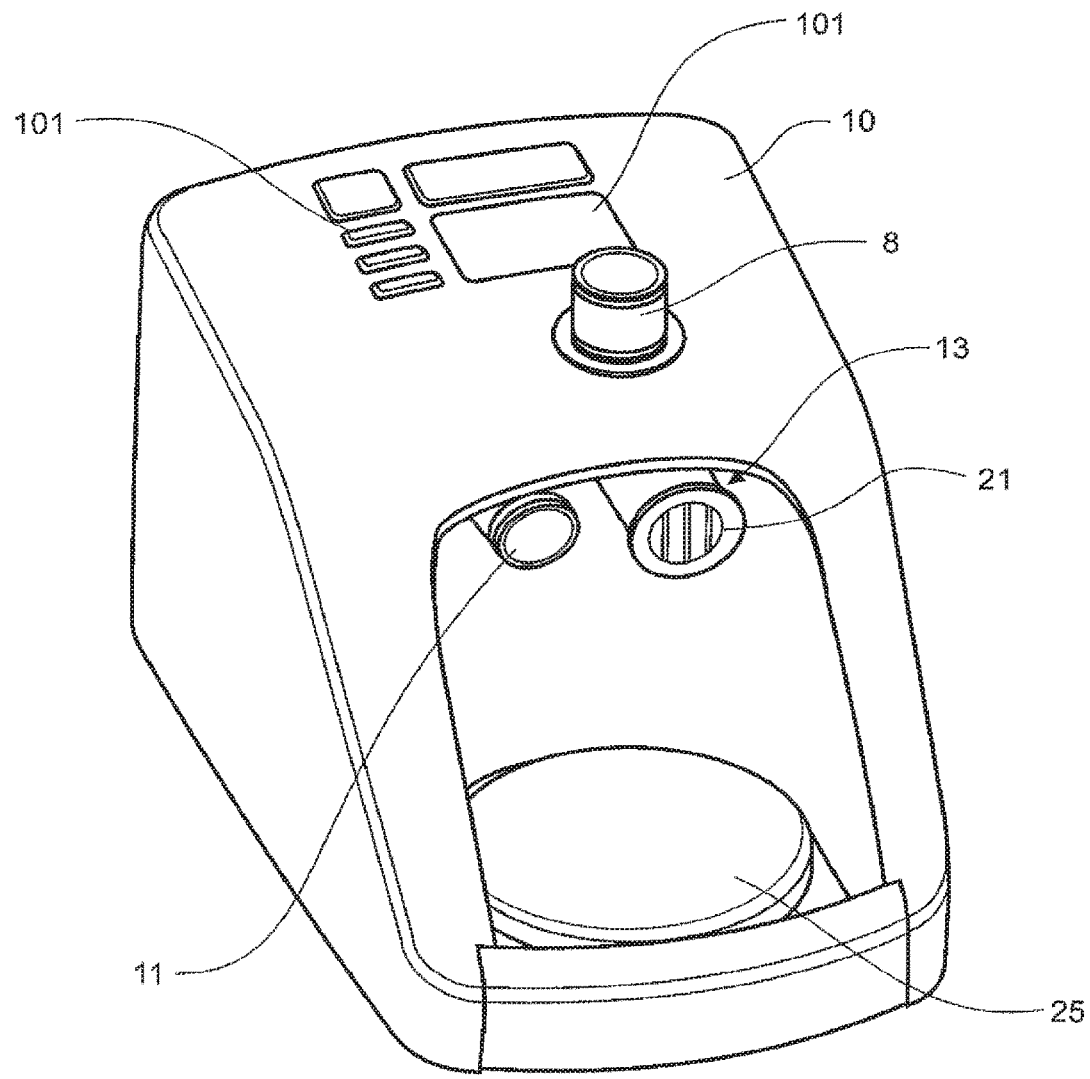
FIG. 4 is a perspective front view of the blower unit of FIGS. 1 to 3, with the chamber removed, and showing a filter over the patient return of the blower unit.

A first disinfection method allows for disinfection of the elbow conduit 12, as described below. The breathing circuit 100 is provided with a first disinfection conduit 14 to allow in particular for disinfection of the elbow conduit 12. The first disinfection conduit 14 is shown in FIG. 3. In order to disinfect the elbow conduit 12, a first end 17 of the first disinfection conduit 14 is connected to the gases supply outlet port 11 and a second end 18 to the patient outlet 8 of the elbow conduit 12 (it should be noted that the humidifier chamber 5 has been removed from the blower unit 4 before the disinfection operation is carried out). The disinfection conduit 14 includes a heating element 19 within, throughout or about the walls of the disinfection conduit 14, and includes connectors at each end to allow connection with the gases supply outlet port 11 and the patient outlet 8.

When the disinfection conduit 14 is connected between the gases supply outlet 11 and the patient outlet 8 as described above, the controller 200 housed within the blower unit 4 is put into a cleaning mode. Dry gases (e.g. air) are circulated through the disinfection conduit 14 and elbow conduit 12, entering the disinfection conduit 14 through the first end 17 connected to the gases supply outlet port 11, and exiting through the second end 18 connected to the patient outlet 8 of the elbow conduit 12, and venting to atmosphere. The circulated gases are heated by the heater 19 in the disinfection conduit 14. In the preferred embodiment, the gases are heated to a temperature of 80° C. However, a temperature of between 60° C. and 90° C. is also considered to be suitable in some circumstances.

The connectors at both ends 17, 18 of the disinfection conduit 14 are preferably pneumatic connectors. At least the second end 18 of the disinfection conduit 14 includes an electrical connector, adapted to mate with a connector on the casing 10, such that the heating element 19 within the conduit 14 is supplied with power from the blower unit 4. In other forms both ends 17, 18 may have both electrical and pneumatic connections.

The controller 200 within the blower unit 4 that controls the heating of the heater plate 25 as described above, also controls the power to the heating element 19, to control the temperature conduit 14.

It is most preferred that the controller 200 of blower unit 4 includes a user setting that causes the blower unit 4 to provide a flow of gases and simultaneously provide power to the heating element 19. The flow of gases would for example be set at a level between 1 and 50 litres per minute. The power provided to the heating element 19 is such that the gases passing through the conduit 14 increase in temperature to 80° C. The controller 200 maintains the power to the heating element 19 to maintain a predetermined temperature inside the elbow conduit 12 for a period of time, in order for the heated dry gases to disinfect the elbow conduit 12. It is preferred that the time is in the region of 20 minutes.

Therefore in use, after a patient has used the breathing circuit 100, and before the next patient uses it, the patient, hospital staff or home care supplier can connect the disinfection conduit 14 to the blower unit 4 as described above, and use the controls to put the device into a cleaning mode. As an example, a person might put the device into a cleaning mode by pressing a button located on the casing 10, pressing the button sending a signal to the controller 200 to activate a routine which causes the controller 200 to provide power to the heating element 19 and the fan to run (so that gases are provided to the disinfection conduit 14), with power provided to the heating element 19 so that it to keep it at a predetermined temperature over a set period of time. In this first disinfection method, or preferred method of disinfecting the device, it is preferred that the surface temperatures inside the elbow conduit 12 reach a minimum of 80° C. for a time period of 20 minutes, and the flow provided for circulation through the elbow conduit 12 is approximately 10 litres per minute. However, other appropriate circulating flows between 1 and 50 litres per minute and other appropriate time periods and temperatures may be used.

Figure 5:
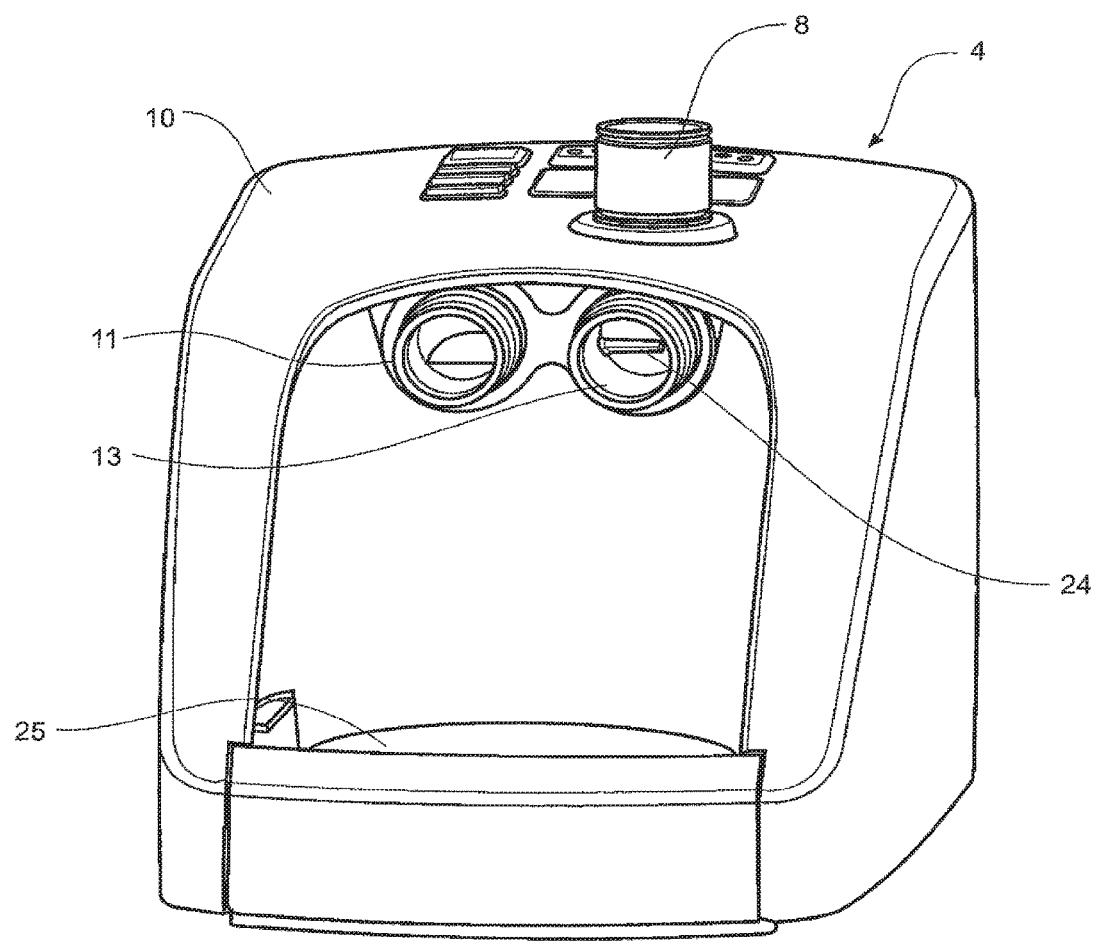
FIG. 5 is a front view of the blower unit of FIG. 4 showing detail of the patient return and a temperature sensor which is located within the patient return

In the most preferred form, a removable exhaust gases filter 20 is placed on the patient return 13 of the elbow conduit 12 prior to the disinfecting routine being run. This filter 20 is shown in more detail in FIGS. 5 and 6. In FIG. 5, a filter housing 21 is shown placed about the patient return 13. The filter housing 21 is preferably made of a plastics material and can be simply removably attached to the patient return 13, and remains on the end of patient return 13 by a friction fit. A circular piece of filter material (not shown in the figures) sits inside the filter housing 21 and therefore occludes the patient return 13, such that in use, gases exiting the patient return 13 are filtered before they exit to the ambient surroundings.

Figure 6:
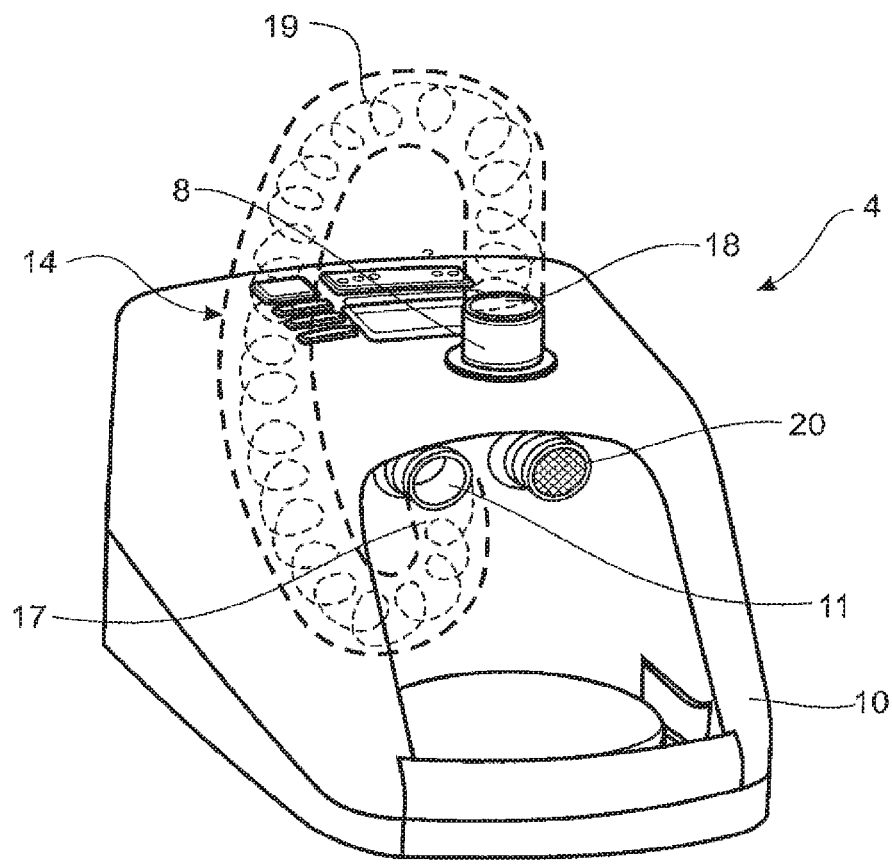
FIG. 6 is a perspective front view of the blower unit of FIG. 3 with the humidifier chamber removed, and a first disinfection conduit which forms part of the apparatus of the present invention connected to the blower unit, FIG. 5 also showing the filter over the patient return.

Referring to FIG. 6, the filter housing 21 is shown in further detail. A projection 22 is provided with the filter 20 and housing 21. This tubular projection 22 sits within the patient return 13 and the filter housing 21 sits about the projection 22 and over the end of the inlet 13. The projection 22 has the purpose of increasing the gases velocity at the point where heated gases are exiting the patient return 13 (when the disinfection conduit 14 is in place as described above and in use). This has the effect of maximising the exhaust temperature of the exiting gases and minimising the temperature drop at the exit point. This ensures there is a high level of disinfection throughout the entire elbow conduit 12. In use, the heated gases flow around the spherical end 23 of the projection 22 down the sides of the tubular inlet end (in the direction of arrows A) through apertures (not shown) in the projection 22 through the filter material 20 and past the filter housing 21 into the ambient surroundings.

Figure 7:
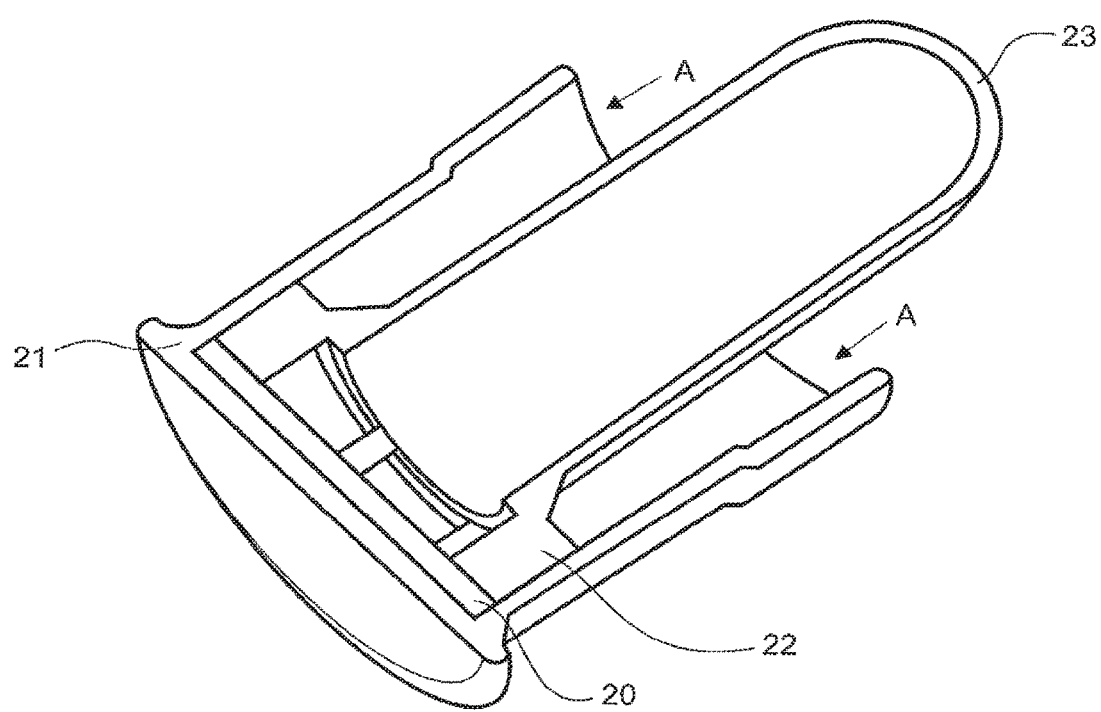
FIG. 7 is a close up cutaway view of the filter which is fitted over the patient return, with detail of the filter cover and a projection that extends within the patient return shown.
Figure 8:
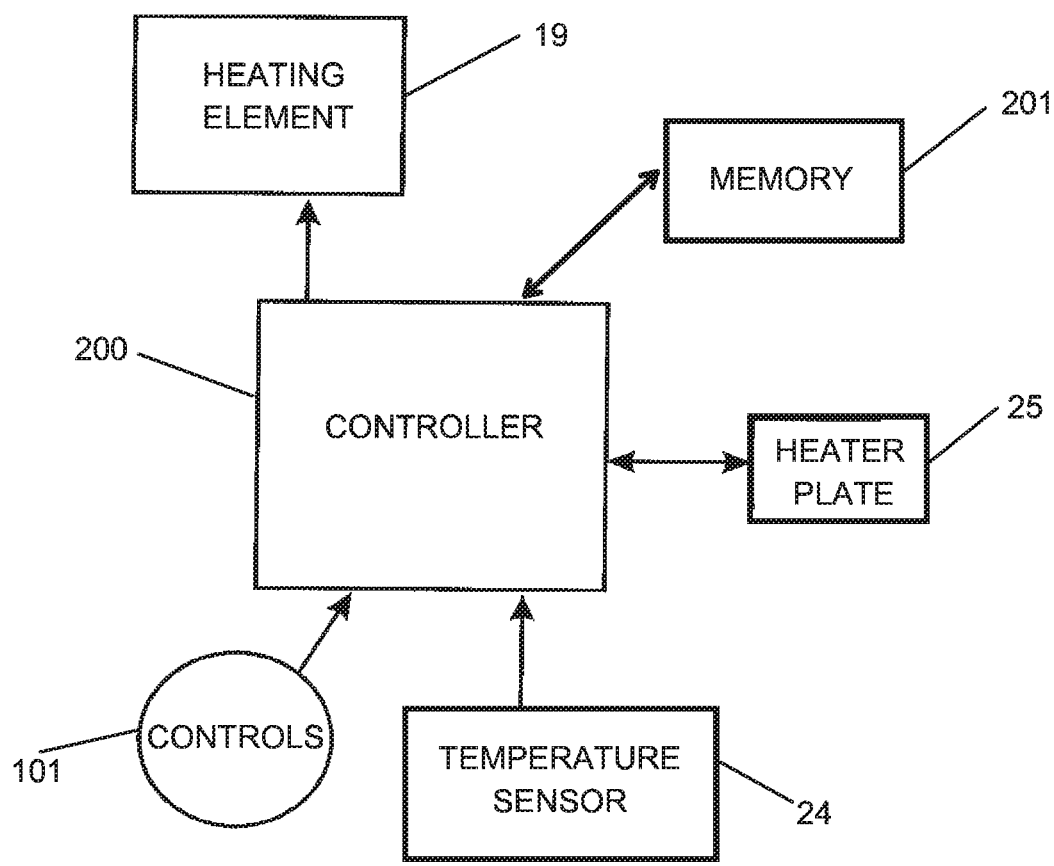
FIG. 8 is a schematic view of the connections between a controller which is enclosed within the blower unit, and elements of the breathing circuit such as the heater plate and the temperature sensor.
Figure 9:
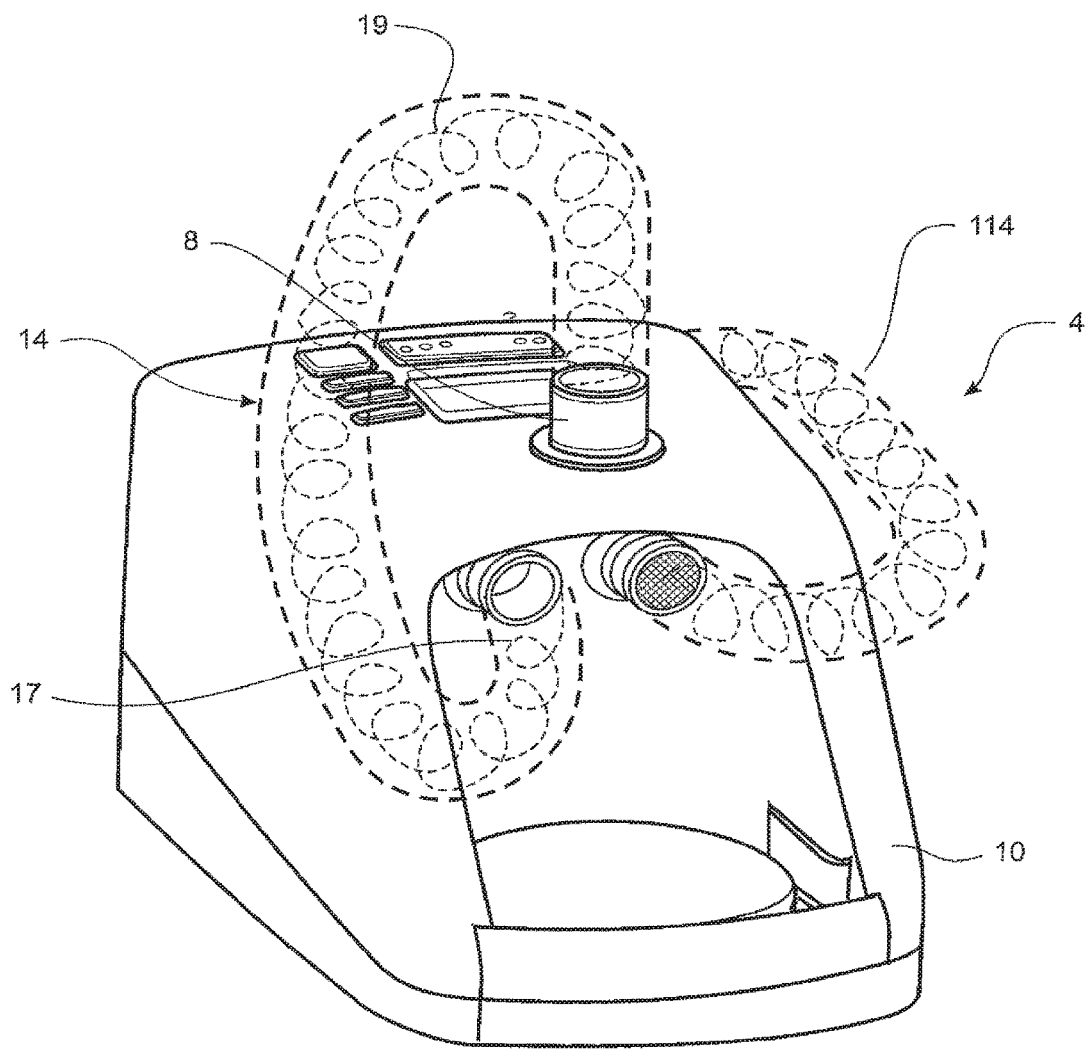
FIG. 9 shows the apparatus of FIG. 6, with a second disinfection conduit shown with one end connected to the patient return, and the body of the second disinfection conduit shown passing around the back of the apparatus to connect to an atmospheric inlet.

In the preferred form of the present invention the elbow conduit 12 has a temperature sensor 24 located within it, as shown in FIG. 7. This sensor measures the temperature of gases travelling through the conduit 12. In particular, in the preferred form, at the start of the disinfection process, the controller 200 performs some checks to ensure the disinfection conduit is correctly connected. Firstly, a check is performed to determine that there is a heated gases flow through the elbow conduit 12 as follows. When the fan inside the blower unit 4 starts to provide a flow of gas, and the heater element 19 of the disinfection conduit 14 is turned on, the temperature of the heated gases flow is measured by the temperature sensor 24. After a predetermined period the heater element 19 is turned off, with the blower unit 4 continuing to provide a flow of gases through the disinfection conduit 14. After a preset or predetermined period of time, the temperature inside the elbow conduit 12 is again measured by the temperature sensor 24. If the temperature has dropped between these measurements, this indicates that there is a fluid connection of gases supply connecting the flow source to the elbow conduit 12.

If a rise in temperature or a fall in temperature between measurements is not detected by the sensor 24, the controller 200 causes an error alarm to be indicated on the housing 10, or audibly relayed, or both, the alarm indicating that the disinfection conduit 14 is not connected to the device 4 correctly.

In the most preferred form, the blower unit 4 also includes an ambient air temperature sensor (not shown) incorporated within it, and adapted to measure the temperature of the surrounding atmospheric air. The controller 200 therefore knows the fan speed (and therefore the flow rate), the ambient temperature (from the ambient temperature sensor), and the gases temperature inside the elbow connector 12 (from temperature sensor 24). Therefore, for any given time period over which the heating element 19 is powered, an expected temperature can be calculated by algorithms loaded into the controller 200, for the heating and non-heating time periods described above. The expected temperature as calculated can then be compared with the actual measured temperature from the temperature sensor 24. If these match or are close to matching (within a tolerance range), then the checks are complete and indicate that the disinfection conduit 14 and heating element 19 are connected and working correctly. The first disinfection method or cleaning mode as described above is then started.

In a variant of the first disinfection method discussed above, the disinfection conduit 14 may be used on a blower unit 4 which does not include an internal temperature sensor inside the elbow conduit 12. In this variant a flow of gases at 10a predetermined rate is caused to pass through the disinfection conduit 14, and a predetermined power level is applied to the heating element 19 within the disinfection conduit 14. The ambient temperature is known from the ambient temperature sensor. The predetermined gases flow and predetermined power applied are determined in such a manner that the internal surface temperatures inside the elbow conduit 12 will easily exceed the temperatures required for high level disinfection for a range of ambient conditions. The predetermined temperature and power are preferably determined from testing and the like, and sub-routines are loaded into the controller 200 which will ensure that the controller 200 provides power to the fan of the blower 4 and the disinfection conduit 14 of suitable levels.

The method of disinfection described above has been validated by an independent laboratory, Toxikon Corporation of Bedford, Mass, USA.

The first method of disinfection as described above is automated so minimal training is required to disinfect the elbow conduit and it is not necessary to dismantle the gases supply and humidification device. Therefore, inadvertent damage to the internal parts of the device is avoided.

Also, during the disinfection period the internal surface temperature of the elbow conduit is continuously monitored by the temperature sensor 24, so each disinfection cycle can be validated and a 'disinfection completed' symbol can be shown on the display at the completion of the process. Alternatively, if the disinfection cycle was not validated a 'failed disinfection' symbol can be displayed to alert a user or operator.

Disinfection of Inspiratory Conduit and Patient Interface

In a second form of the present invention a second disinfection method, or second method of disinfecting an inspiratory conduit 3 and patient interface 2 is disclosed.

The inspiratory conduit 3 of the breathing circuit 100 preferably includes heater wires 7 within it. The wires 7 within the conduit 3 can make it difficult or dangerous to clean and disinfect the conduit 3. Therefore, prolonged use of the conduit 3 by a patient 1 results in high microbial contamination inside the conduit 3. Consequently there is a danger of infection of the patient 1 from continual use of the conduit 3. Therefore, for home use where patients 1 are reusing the inspiratory conduit 3 and patient interface 2 over a substantial period it is preferable to provide a method of cleaning and disinfecting the conduit 3 and patient interface 2.

As shown in FIG. 1, one end of inspiratory conduit 3 is connected to the patient outlet 8. The patient interface 2 is connected to the other end of the conduit 3.

In order to disinfect the conduit 3, or both of the conduit 3 and the patient interface 2, dry heat is forced through the conduit 3 to heat and dry the conduit 3 such that bacteria and microbes are killed and cannot multiply. This is carried out when the patient 1 is not using the system 100. This is achieved as follows: After a patient 1 has completed their treatment (for example, each morning) the patient 1 removes the patient interface 2 and then empties the humidification chamber 5, replacing the chamber 5 on the blower unit 4. The user or patient 1 then activates the second disinfection method, for example by pressing a button on the housing 10 thereby activating a control sequence or algorithm pre-loaded into the controller 200. Other mechanisms for activating the sequence may be provided—for example, the device may automatically activate the conduit disinfecting control sequence after a certain predetermined time period has elapsed after completion of treatment. Removal of the patient interface 2 triggers the start of this predetermined time period.

Once the chamber 5 has been replaced on the heater plate 25, the controller 200 powers the plate 25 to maintain heat to the humidifying chamber 5, and the blower unit 4 supplies gases through the chamber 5, via the gases supply outlet 11 and the patient outlet 8. it can be seen that a supply of heated dry gases pass through the chamber 5 to the conduit 3. At the same time, the power to the heater wires 7 is maintained to provide additional heat to the gases within the conduit 3. In the most preferred form, the gases are heated to approximately 40° C., but can be as high as 75° C. or more. The exit temperature from the conduit 3 is between 40° C. and 75° C. The disinfecting and heating sequence preferably continues for between 30 and 120 minutes. In the most preferred form of the second disinfecting method, the humidification chamber heater plate 25 heats the gases passing through the chamber 5 until the temperature of the gases in the patient return 13 reaches 40° C. The heater wires 7 in the heated breathing conduit 3 maintain the temperature of the gases passing through the conduit 3. If required, a third temperature sensor can be located at the patient end of the conduit to measure the temperature of the gases exiting the conduit 3 and the patient interface 2. This third temperature sensor will indicate when the gases have reached a temperature of approximately 50° C. In variations it is possible that this temperature may be raised to as high as 70° C.

In other variations of this method, a cap is placed on the patient end of the heated breathing conduit 3 (in place of the patient interface 2). The cap allows the heated gases to build up in the conduit thereby increasing the effectiveness of the disinfection process. Another purpose of the cap is to ensure that patient 1 is not wearing the patient interface 2. In the preferred form, the controller 200 is pre-loaded with flow and pressure characteristics for a range of users (to give maximum and minimum values of typical pressure and flow rates when the system 100 is being used by a patient 1). The pressure and flow characteristics when the cap is on the distal end of the conduit 3 will be very different to the 'in use' characteristics when the patient interface 2 is attached to the end of the conduit 3. If the pressure and flow characteristics are well outside the 'in use' parameters, this is indicative that the patient 1 is not wearing the interface 2 and that it is safe to heat the air in the heated breathing conduit to temperatures well above safe gas breathing temperatures. This greatly improves the efficacy of the disinfection process.

In other variations, the patient interface 2 is left in place at the distal end of the conduit 3 and is also exposed to the heated and dry gases.

In further forms the patient interface 2 can be contained or housed in a receptacle while the second disinfection method is carried out. This allows increased heat build up to occur in the patient interface 2 during the second disinfection process. Again, this increases the effectiveness of disinfection. If the interface 2 is contained in a receptacle, it can be ensured that a patient 1 cannot be using the interface 2 for breathing, and the controller 200 can detect there is no patient connected, again because of the different pressure and flow characteristics. The heated breathing conduit 3 can then be heated to temperatures well above safe gases breathing temperatures. Again this improves the efficacy of the disinfection process.

The purpose of this disinfection process is to increase the useable life of the heated breathing conduit 3 by lowering microbial contamination on the inside surfaces the gases pass over. If the heated breathing conduit 3 is not cleaned regularly (this being difficult to achieve with conduits that include an internal heating wire 7), microbes can build to a level so that the inside of the surfaces of the conduit become colonised with bacteria. This lowers the useful life of the conduit 3, making treatment more inconvenient for the patient 1.

Tests were carried out on a heated breathing conduit in normal use for 2 months at home by patients with no disinfection process. The conduits were then tested for contamination. The results were that contamination within the conduits had reached a level of bacterial contamination that made the conduits unsafe for use.

Further tests were also carried out with identical heated breathing conduits used under the same conditions for 2 months as described above. The conduits were then processed with the dry heat disinfection method described above. The result was that bacterial contamination was at a level such that the conduits could continue to be used safely—the level of contamination was lower compared to the conduits that had not been treated.

This disinfection method by dry heat shows that bacterial contamination can be effectively lowered to a level that the conduits could continue to be used by patients.

For both the first and second disinfection methods outlined above, it is most preferred that the controller 200 counts and logs the number of disinfection cycles that have taken place, storing these in the memory 201 so that a user can access these via the display or by downloading these, or similar. The controller 200 will be able to recognise which of the disinfection methods is taking place either by noting which cycle has been selected by a user, or by comparing the flow and temperature characteristics as measured, with preloaded parameters indicative of a particular cycle. It is also preferred that the controller 200 distinguishes between successful and failed disinfection cycles, logging these separately.

Disinfection of the Blower Unit

Another problem that has been noted with the use of breathing circuits such as the one described above is that of microbial build-up on the interior parts (i.e. the internal gas path or gas passages from the atmospheric inlet 9, through the fan, to the gases supply outlet port 11) of the blower unit 4. The disinfection method described above for the preferred embodiment can be varied in the manner described below in order to disinfect the internal gas path or gas passages of the blower unit 4 or at least delay microbial build-up.

In this alternative (or third) disinfection method, a second disinfection conduit 114 is used as well as the first disinfection conduit 14 described above. One end of the disinfection conduit 114 is connected to the humidifier end of the patient return 13, to receive the heated gases passing out of the blower unit 4 when the first disinfection method outlined above is being carried out. The second end of conduit 114 is connected at or close to the atmospheric inlet 9. In the preferred form, atmospheric inlet 9 is adapted so that a pneumatic connection can be formed between the second end of conduit 114 and the atmospheric inlet 9—for example by having the two elements mutually shaped to connect in this manner. It is preferred that this connection is made in such a manner that the second end is not completely sealed to or around the atmospheric inlet 9—around 5% of the gases entering the atmospheric inlet 9 will be from atmosphere, with the remaining 95% of the gases entering the atmospheric inlet 9 being recirculating gases from the conduit 114, the 5% air from atmosphere mixing with the 95% hot air from the conduit 114. The hot air then passes through the internal gas path of the blower unit 4, and dries and disinfects the internal gas path in a similar manner as has been described above for the first and second disinfection methods. As for the first and second disinfection methods outlined above, the controller 200 logs the number of cycles that have occurred, distinguishing between successful and failed cycles.

Use of a Disinfection Agent to Assist Disinfection

The first, second and third disinfection methods outlined above use hearted dry air to disinfect, or at least reduce the incidence of, microbial build-up in elements of the breathing circuit 100. It has been found that using a disinfection agent in the gases state to assist this process is beneficial and assists in the disinfection process. This shall be described in relation to the second disinfection methods which has been described above.

In this variant of the second method, the user removes and empties the chamber 5, as for the third disinfection method outlined above. However, the user then partly fills the chamber 5 with a disinfecting agent in a liquid state, and replaces the chamber 5 on the blower unit 4. The chamber 5 is then heated by the plate 25. The contents of the chamber 5—i.e. the disinfecting agent—is heated and begins to vaporise in a similar manner to how the water 6 would vaporise if the system 100 was in use. The vapour rises into the vapour space in the chamber 5 above the liquid disinfecting agent. A stream of gases is entering the chamber through inlet 26, and the vapour mixes with this stream of gases before being carried out of the chamber 5 through the chamber outlet 15, along the patient return 13. If a conduit 3 (and possibly an interface 2) are connected to the patient outlet 8, the vapour will pass along this before exiting to atmosphere. As this vapour is a vapour form of a disinfecting agent, as it passes along the conduit 3 and interface 2, it will assist in reducing the incidence of microbial or bacterial build-up. It is preferred when carrying out this method that the conduit 3 only is disinfected in this manner, and that the cap is connected to the end of the conduit to ensure that patient 1 is not wearing the patient interface 2.

In the most preferred form, the disinfecting agent is a 3-6% solution of hydrogen peroxide in water, or alternatively, a 2-4% solution of formaldehyde can be used. These are the most preferred concentration, although other concentrations can be used.

What is claimed is:

1. A breathing assistance apparatus adapted to deliver humidified gases to a patient, said breathing assistance apparatus comprising:
    a breathing assistance apparatus housing comprising an inlet;
    a pressurized gases supply within said breathing assistance apparatus housing and in fluid communication with said inlet, the pressurized gases supply comprising a blower;
    a gases supply outlet port in said breathing assistance apparatus housing, said gases supply outlet port in fluid connection with said blower; and
    a controller housed within said breathing assistance apparatus housing and communicating with a memory, said controller controlling said blower,
    a connection conduit comprising a patient return end and a patient outlet end configured to be connected to an inspiratory conduit in a first mode and to a disinfection conduit in a cleaning mode;
    wherein the controller is configured to receive device data associated with the connection conduit;

said breathing assistance apparatus being operable by said controller in the cleaning mode, the controller configured to compare the device data received during the cleaning mode to pre-loaded data corresponding to the cleaning mode to determine a cleaning mode indication, the controller being configured to store the cleaning mode indication that a cleaning cycle has taken place in a log in said memory, wherein the blower circulates gases during the cleaning mode.

2. A breathing assistance apparatus according to claim 1, wherein said breathing assistance apparatus is configured to be operated in said cleaning mode by said controller following user activation.

3. A breathing assistance apparatus according to claim 1, wherein said controller is configured to count a number of cleaning cycles that have taken place and store said number in said memory.

4. A breathing assistance apparatus according to claim 1, wherein said controller is configured to provide said log to a user via a display or download.

5. A breathing assistance apparatus as claimed in claim 1, wherein the cleaning mode indication comprises an indication of failed cleaning cycles and successful cleaning cycles.

6. A breathing assistance apparatus according to claim 5, wherein said controller is configured to store indications of said failed cleaning cycles and said successful cleaning cycles separately in said memory.

7. A breathing assistance apparatus according to claim 1, wherein in said cleaning mode said breathing assistance apparatus is configured to supply a heated flow of gases through a disinfection conduit having a heating element.

8. A breathing assistance apparatus according to claim 7, wherein said breathing assistance apparatus comprises a setting in which said controller is configured to cause said pressurized gases supply to provide a flow of gases while also causing said heating element to simultaneously provide heat to said heated flow of gases.

9. A breathing assistance apparatus according to claim 8, wherein said flow of gases has a flow rate in a range of 1 to 50 L/min.

10. A breathing assistance apparatus according to claim 1, wherein said gases supply outlet port is configured to make removable fluid connection with an inlet of a humidification chamber.

11. A breathing assistance apparatus according to claim 1 further comprising a patient return in said breathing assistance apparatus housing, said patient return configured to make removable fluid connection with an outlet of a humidification chamber.

12. A breathing assistance apparatus according to claim 11, wherein said patient return is fixed in said breathing assistance apparatus housing of said breathing assistance apparatus.

13. A breathing assistance apparatus according to claim 11 further comprising a patient outlet in fluid connection with said patient return, said patient outlet configured to make removable fluid connection with a breathing conduit.

14. A breathing assistance apparatus according to claim 13, wherein said controller is configured to operate said breathing assistance apparatus in said cleaning mode when a first end of a disinfection conduit is connected to said gases supply outlet port and a second end of said disinfection conduit is connected to said patient outlet such that a gases flow through said disinfection conduit has not passed through said humidification chamber prior to flowing through said disinfection conduit, and said controller is configured to control power to a heating element of said disinfection conduit to maintain said gases flow through said disinfection conduit above a predetermined temperature over a set period of time.

15. A breathing assistance apparatus according to claim 14, wherein said set period of time is approximately 20 minutes.

16. A breathing assistance apparatus according to claim 14, wherein said gases flow through said disinfection conduit is heated to a temperature between 60° C. and 90° C.

17. A breathing assistance apparatus according to claim 13 further comprising a temperature sensor located at or near said patient return and configured to sense a temperature of gases flowing to said patient outlet in use.

18. A breathing assistance apparatus according to claim 11 further comprising a disinfection conduit.

19. A breathing assistance apparatus according to claim 18, wherein said disinfection conduit comprises an electrical connector positioned at or near at least one end of said disinfection conduit.

20. A breathing assistance apparatus according to claim 19, wherein said disinfection conduit comprises a heating element and said controller is configured to control said heating element through said electrical connector.

21. A breathing assistance apparatus according to claim 18 further comprising a breathing conduit configured to make removable connection with a patient outlet of said breathing assistance apparatus, wherein said disinfection conduit is configured to make removable connection with said patient outlet, and wherein said breathing conduit must be removed from said patient outlet before said disinfection conduit is connected to said patient outlet.

22. A breathing assistance apparatus according to claim 1, further comprising a sensor, wherein the device data received by the controller is from the sensor.

23. A breathing assistance apparatus according to claim 22, wherein the sensor is a temperature sensor, and wherein the device data is temperature data indicative of a temperature of gases passing through the connection conduit and/or an internal surface of the connection conduit.

24. The breathing assistance apparatus according to claim 1, wherein the device data comprises an indication of power drawn by the blower, and wherein the controller is configured to estimate a gas flow rate through the breathing assistance apparatus using the indication of power drawn by the blower.

25. The breathing assistance apparatus according to claim 24, wherein the controller is configured to calculate the gas flow rate through the breathing assistance apparatus by comparing the indication of power drawn by the blower to pre-stored values in a look-up table.

* * * * *

UNITED STATES PATENT AND TRADEMARK OFFICE
CERTIFICATE OF CORRECTION

PATENT NO. : 10,512,702 B2  
APPLICATION NO. : 15/388481  
DATED : December 24, 2019  
INVENTOR(S) : Kevin Peter O'Donnell Page 1 of 1

It is certified that error appears in the above-identified patent and that said Letters Patent is hereby corrected as shown below:

On the Title Page

Column 1, item (72), Inventors, Line 5, delete "Friederich" and insert --Friedrich--.

In the Specification

Column 3, Line 57, delete ""patient" and insert --patient--.

Column 6, Line 16, delete "return" and insert --return.--.

Column 11, Line 19 approx., delete "Mass," and insert --Mass.,--.

In the Claims

Column 16, Line 22 (approx.), Claim 18, delete "claim 11" and insert --claim 1--.

Signed and Sealed this  
Thirty-first Day of March, 2020

Andrei Iancu  
*Director of the United States Patent and Trademark Office*